(12) United States Patent
Kitadai

(10) Patent No.: US 9,101,630 B2
(45) Date of Patent: Aug. 11, 2015

(54) USE OF PDGF-R INHIBITORS FOR THE TREATMENT OF LYMPH NODE METASTASIS OF GASTRIC CANCER

(76) Inventor: Yasuhiko Kitadai, Hiroshima (JP)

( * ) Notice: Subject to any disclaimer, the term of this patent is extended or adjusted under 35 U.S.C. 154(b) by 0 days.

(21) Appl. No.: 13/695,044

(22) PCT Filed: Apr. 28, 2011

(86) PCT No.: PCT/JP2011/060894
§ 371 (c)(1),
(2), (4) Date: Jan. 18, 2013

(87) PCT Pub. No.: WO2011/136399
PCT Pub. Date: Nov. 3, 2011

(65) Prior Publication Data
US 2013/0144059 A1   Jun. 6, 2013

(30) Foreign Application Priority Data
Apr. 30, 2010 (EP) .................................. 10161692

(51) Int. Cl.
*A61K 31/506* (2006.01)
*A61K 31/404* (2006.01)
*C07D 403/14* (2006.01)
*A61K 31/4439* (2006.01)

(52) U.S. Cl.
CPC ............. *A61K 31/506* (2013.01); *A61K 31/404* (2013.01); *A61K 31/4439* (2013.01)

(58) Field of Classification Search
CPC ... C07D 403/14; A61K 31/506; A61K 31/404
See application file for complete search history.

(56) References Cited

FOREIGN PATENT DOCUMENTS

WO    2006132930    12/2006
WO    2008/155387   12/2008

OTHER PUBLICATIONS

American Chemical Society (ACS). STN CAS Registry Database.*
American Chemical Society (ACS). © 2001. STN CAS Registry Database.*
Sakurama et al.; "Establishment of a lymph node metastasis model from subcutaneous tumors of gastrointestinal stromal tumor model cells", (2009) Oncology Reports 21: 407-411.
Heinrich et al.; "PDGFRA Activating Mutations in Gastrointestinal Stromal Tumors", (2003) Science 299: 708-710.
Zhang et al., "Gastrointestinal stromal tumor of stomach with inguinal lymph nodes metastasis: A case report", (2010) World Journal of Gastroenterology 16(14): 1808-1810.
Zhang et al., "Gastrointestinal stromal tumor of stomach with inguinal lymph nodes metastasis: A case report"; World Journal of Gastroenterology, (Apr. 14, 2010), 16(14): 1808-1810.
Canda et al. "Gastrointestinal stromal tumor of the stomach with lymph node metastasis"; World Journal of Surgical Oncology, (Sep. 5, 2008), 6(97): 1-5.
Coo et al. "PDGF-BB induces intratumoral lymphangiogenesis and promotes lymphatic metastasis"; Cancer Cell, (Oct. 2004), 6: 333-345.
Journal of Japanese Society of Gastroenterology; (2006), 103: Special Edition, A409.
Kodama et al., Proceedings of the Japanese Cancer Association (2008), 67: 312.

* cited by examiner

*Primary Examiner* — Noble Jarrell
*Assistant Examiner* — John S Kenyon
(74) *Attorney, Agent, or Firm* — Saliwanchik, Lloyd & Eisenschenk

(57) ABSTRACT

The present invention relates to the use of PDGF-R inhibitors for the treatment of lymph node metastasis of gastric cancers and to a method of treating mammals including humans suffering from gastric cancer.

6 Claims, 3 Drawing Sheets

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PDGF-B forward primer

<400> SEQUENCE: 1
cgagttggac ctgaacatga                                                    20

<210> SEQ ID NO 2
<211> LENGTH: 20
<212> TYPE: DNA
<213> ORGANISM: Artificial Sequence
<220> FEATURE:
<223> OTHER INFORMATION: PDGF-B reverse primer

<400> SEQUENCE: 2
gtcaccgtgg ccttcttaaa                                                    20

<210> SEQ ID NO 3
<211> LENGTH: 23
<212> TYPE: DNA
<213> ORGANISM: Artificial Sequence
<220> FEATURE:
<223> OTHER INFORMATION: PDGF-R beta forward primer

<400> SEQUENCE: 3
```

```
agctacccct caaggaatca tag                                              23

<210> SEQ ID NO 4
<211> LENGTH: 23
<212> TYPE: DNA
<213> ORGANISM: Artificial Sequence
<220> FEATURE:
<223> OTHER INFORMATION: PDGF-R beta reverse primer

<400> SEQUENCE: 4
ctctggtgga tggattaaga ctg                                              23

<210> SEQ ID NO 5
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 5
atcatccctg cctctactgg                                                  20

<210> SEQ ID NO 6
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 6
ccctccgacg cctgcttcac                                                  20
```

USE OF PDGF-R INHIBITORS FOR THE TREATMENT OF LYMPH NODE METASTASIS OF GASTRIC CANCER

TECHNICAL FIELD

The present invention relates to the use of PDGF-R inhibitors for the treatment of lymph node metastasis of gastric cancers and to a method of treating mammals including humans suffering from gastric cancer.

BACKGROUND ART

Lymph node metastasis is a common clinical finding in many human cancers and is associated with both aggressive disease and poor prognosis. Gastric cancer is one of the most frequent malignancies in the world. The major cause of mortality is metastasis, which relies on de novo formation of blood and lymphatic vessels (Fidler I J. Nat Rev Cancer 2003; 3: 453-8). Although induction of tumor angiogenesis is known to be a complex process that involves the interplay of a dozen or more tumor-derived growth factors (Carmeliet P, Jain R K. Nature 2000; 407: 249-57), it is poorly understood how tumors induce lymphangiogenesis. Among known lymphangiogenic factors, the best-characterized growth factors are vascular endothelial growth factor (VEGF)-C and VEGF-D. A range of lymphangiogenic factors produced by tumor cells, endothelial cells and stromal cells has recently been identified. These include VEGF-A, and members of the hepatocyte growth factor (HGF) and angiopoietin (Ang) families (Gale N W, et al., Dev Cell 2002; 3: 411-23; Kajiya K, et al. Embo J 2005; 24: 2885-95; Hirakawa S, et al., J Exp Med 2005; 201: 1089-99).

Members of the PDGF (platelet derived growth factor) family are often expressed at high levels in many malignant tissues. The PDGF family consists of five isoforms, -AA, -AB, -BB, -CC and -DD. Their biological activities are mediated by three forms of the tyrosine kinase receptor encoded by two gene products, PDGF-Rα and -Rβ. PDGF-Rα binds all possible forms of PDGF except PDGF-DD, whereas PDGF-Rβ preferentially binds PDGF-BB. PDGFs have been found to induce tumor growth by directly stimulating growth of certain types of tumor cells, to stimulate angiogenesis, to recruit pericytes and to control the interstitial fluid pressure in stroma, influencing transvascular transport of chemotherapeutic agents in a paracrine manner.

SUMMARY OF INVENTION

Solution to Problem

Surprisingly, it was now found that PDGF-R inhibitors can be used for the treatment the lymph node metastasis of gastric cancers.

In a broader sense, the present invention provides for a method of treating gastric cancer by administering compounds inhibiting the PDGF signaling pathway to patients in need thereof.

Expression levels of PDGF-B and PDGF-Rβ mRNAs in human gastric carcinoma. mRNA expression of PDGF-B and PDGF-Rβ was examined by quantitative real-time PCR as described in the Examples. The relative expression levels (T/N ratio) of PDGF-B and PDGF-Rβ are shown according to node status in FIG. 1A. Patients with positive lymph nodes showed significantly greater expression of PDGF-B and PDGF-Rβ than was shown by node-negative patients (P=0.03 and P<0.001, respectively). We also examined the relation between PDGF-B and PDGF-Rβ mRNA expression and histologic type of human gastric carcinoma because diffuse-type gastric carcinoma is known to have abundant stroma and a high probability of lymph node metastasis. Expression of PDGF-B and PDGF-Rβ was significantly greater in patients with diffuse-type gastric carcinoma than in those with intestinal-type gastric carcinoma (P=0.02 and P=0.01, respectively) (FIG. 1B). Patients with positive lymph nodes showed significantly greater expression of PDGF-B and PDGF-Rβ than that of node-negative patients.

Expression of PDGF-B and PDGF-Rβ in human gastric carcinoma cell lines growing in culture. The expression of PDGF-B and PDGF-Rβ in four human gastric carcinoma cell lines derived from different histological types was examined as described in the Examples. MG63 cells were used as a positive control for PDGF-R expression. The results of real-time PCR and Western blot analysis are shown in FIG. 2. Under culture conditions, expression of PDGF-B mRNA was found in all of the gastric cell lines, albeit at different levels. PDGF-Rβ was not expressed by the cultured gastric carcinoma cell lines.

Treatment of human gastric carcinoma growing in mouse stomachs. The effects of imatinib, PDGF-Rβ thyrosine kinase inhibitor, on lymphatic vessels in tumors growing up from implantation of TMK-1 human gastric carcinoma cells into the stomachs of nude mice was determined as described in the Examples. The tumors treated with imatinib mesylate had reduced areas of lymphatic vessels in comparison to areas of lymphatic vessels in control tumors (P<0.05) (FIG. 5).

Tumor blood vessels have been shown to differ morphologically from their normal counterparts. The endothelial cells are structurally and functionally abnormal and can acquire cytogenetic abnormalities while in the tumor microenvironment. Tumor lymphatic vessels appear to be structurally disorganized, tortuous and leaky (Cao R, et al. Cancer Cell 2004; 6: 333-45). These leaky tumoral lymphatics could provide a vulnerable structural basis for tumor cell invasion into the lymphatic system. Like tumor blood cells, tumor-associated lymphatic vessels have been recently shown to have differentially expressed genes. Clasper et al. compared gene expression of purified lymphatic endothelial cells from highly metastatic fibrosarcoma and from dermal tissue (Cancer Res 2008; 68: 7293-303). They found differential expression of some 792 genes that code for a variety of proteins including components of endothelial junctions, sub-endothelial matrix, and vessel growth/patterning. In the orthotopic gastric cancer model used in the Examples, Lyve-1-positive lymphatic vessels were shown to express PDGF-Rβ, whereas not all lymphatic vessels expressed PDGF-Rβ. PDGF-Rβ was expressed occasionally on lymphatic endothelial cells, especially on enlarged and tortuous lymphatic vessels located immediately adjacent to tumor nests, whereas lymphatic vessels in normal tissue or intratumoral small lymphatic vessels did not express PDGF-Rβ. In general, tumor cells in a neoplasm are biologically heterogeneous, and their phenotype can be modified by the organ microenvironment (Fidler I J, Poste G., Semin Oncol 1985; 12: 207-21). Our data demonstrate that tumor-associated lymphatic vessels are biologically heterogeneous and that interplay between lymphatic vessels and tumor cells has a more significant effect on the endothelial phenotype than previously known. Additionally, blockade of PDGF-Rβ signaling by oral administration of the PDGF-R tyrosine kinase inhibitor imatinib significantly reduced the area of lymphatic vessels in orthotopic mouse model of gastric cancer used herein. Together, these findings indicate that PDGF-Rβ is preferentially expressed by activated, proliferating lymphatic endothelium but not by quiescent lymphatic vessels in normal tissue, a finding with important implications for the potential therapeutic use of targeted PDGF-Rβ-blocking strategies. In conclusion, it was found that PDGF-B secreted by tumor cells and PDGF-Rβ expressed by stromal cells including lymphatic endothelial cells to be associated with lymphatic metastasis in gastric carcinoma. Thus, inhibition or blockage of PDGF-induced lymphangiogenesis is a reasonable approach to prevention and treatment of lymphatic metastasis.

DESCRIPTION OF EMBODIMENTS

Figure 1:
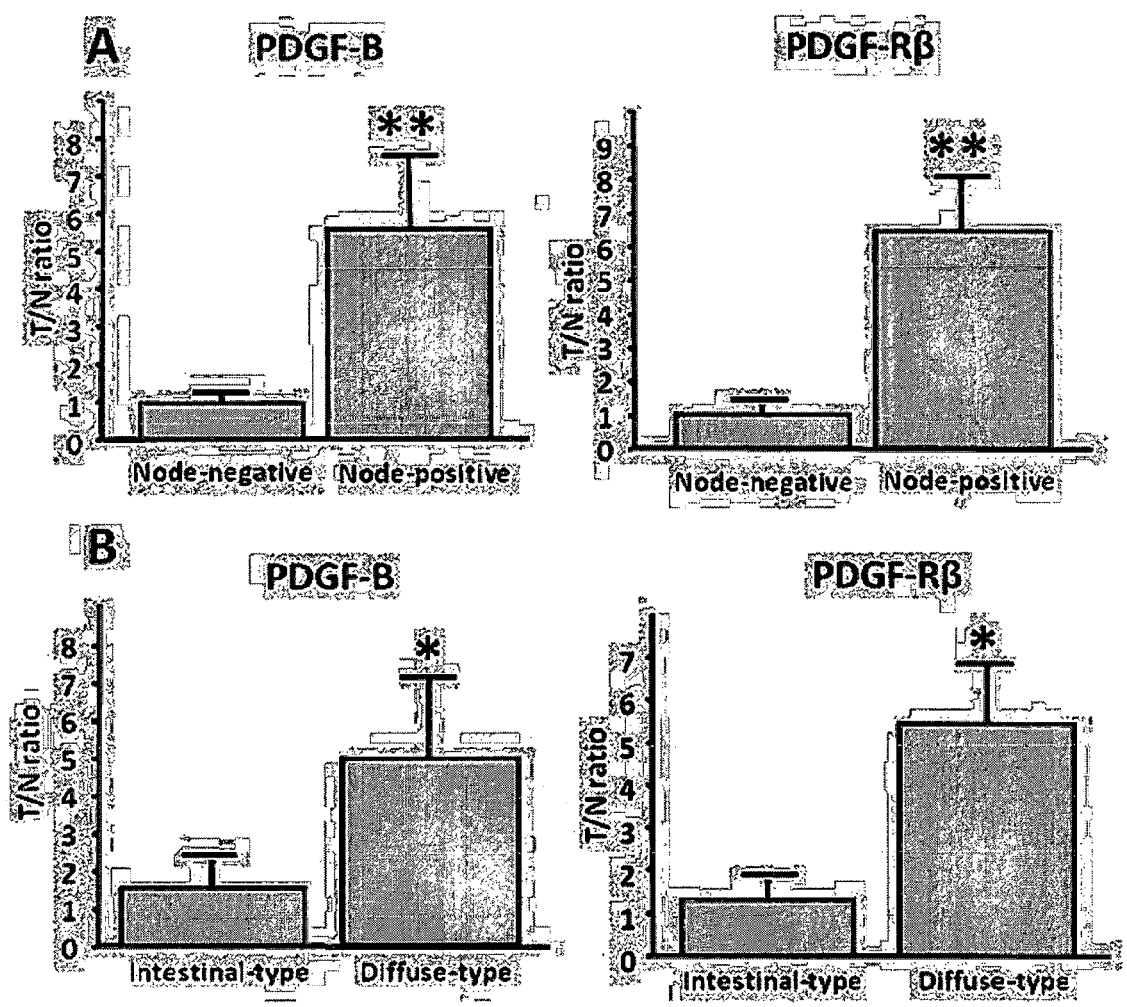
FIG. 1 Results of quantitative real-time PCR for mRNA expression of PDGF-B and PDGF-Rβ of human gastric carcinoma specimens. (A) PDGF-B and PDGF-RβmRNA expression levels in relation to regional lymph node status. (B) PDGF-B and PDGF-Rβ mRNA expression levels in relation to histologic type of human gastric carcinoma. Patients with diffuse-type gastric carcinoma showed significantly greater expression of PDGF-B and PDGF-Rβ than did those with intestinal-type gastric carcinoma. All values were normalized against GAPDH and then against the level of each of these RNAs found in normal areas. The mRNA ratio between gastric carcinoma tissues (T) and corresponding normal mucosa (N) was calculated and expressed as the T/N ratio. Values shown are mean±SE. *P<0.05, **P<0.01.
Figure 2:
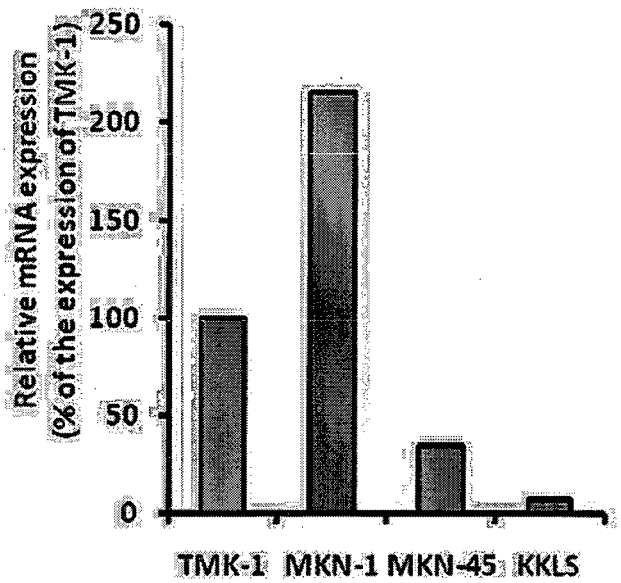
FIG. 2 Expression of PDGF-B and PDGF-Rβ in gastric carcinoma cell lines. (A) Gastric cancer cell lines constitutively expressed mRNA for PDGF-B subunit at various levels. (B) PDGF-Rβ was not expressed by the cultured gastric carcinoma cell lines.
Figure 2:
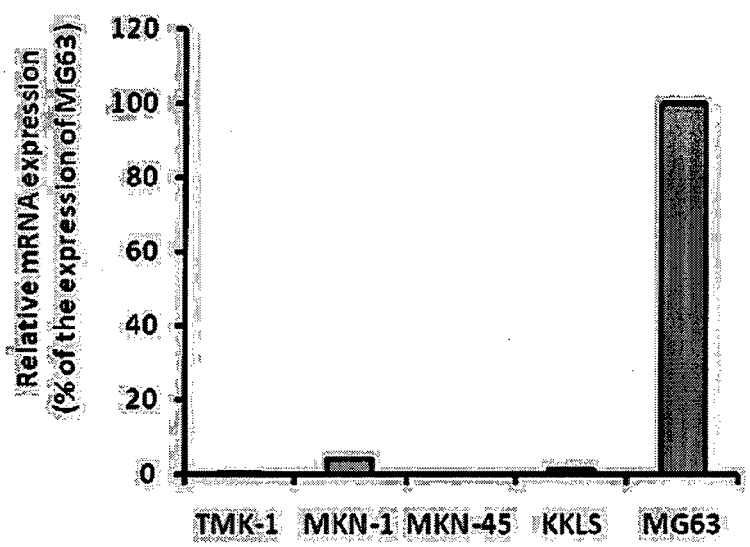

Hence, the present invention relates in one aspect to the use of PDGF-R inhibitors for the treatment of lymph node metastasis of gastric cancers.

The expression "PDGF-R inhibitors" as used herein especially includes, but is not limited to 4-(4-methylpiperazin-1-ylmethyl)-N-[4-methyl-3-(4-pyridin-3-yl)pyrimidin-2-ylamino)phenyl]-benzamide (also known as "imatinib"), 4-methyl-3-[[4-(3-pyridinyl)-2-pyrimidinyl]amino]-N-[5-(4-methyl-1H-imidazol-1-yl)-3-(trifluoromethyl)phenyl] benzamide (also known as "nilotinib") axitinib (AG013736), and sunitinib (SUTENT™) or pharmaceutically acceptable salts thereof, respectively.

For the purpose of the present invention, preference is given in one embodiment to imatinib mesylate and nilotinib monohydrochloride monohydrate. In a further embodiment of the instant invention, preference is given to axitinib and sunitinib (SUTENT™) or pharmaceutically acceptable salts thereof, respectively.

The terms "treatment" or "therapy" refer to the prophylactic or preferably therapeutic (including but not limited to palliative, curing, symptom-alleviating, symptom-reducing) treatment of the diseases disclosed herein. It means in particular a delay or stop of progression of lymph node metastasis.

The preparation of imatinib and its use, especially as an anti-tumor agent, are described in Example 21 of EP-A-0 564 409 and U.S. Pat. No. 5,521,184, both incorporated by reference.

Pharmaceutically acceptable salts of imatinib are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid.

The monomethanesulfonic acid addition salt of imatinib (also known as "imatinib mesylate") and preferred crystal forms thereof, e.g. the β-crystal form, are described in WO99/03854. Depending on species, age, individual condition, mode of administration, and the clinical picture in question, effective doses, for example oral daily doses of about 100-1000 mg, preferably 200-600 mg, especially 400 mg of imatinib, are administered to warm-blooded animals of about 70 kg body weight. For adult patients a starting dose corresponding to 400 mg of imatinib I free base daily can be recommended for oral delivery.

Possible pharmaceutical preparations, containing an effective amount of imatinib or a pharmaceutically acceptable salt thereof are also described in WO99/03854.

Imatinib (as mesylate salt, Glivec™/Gleevec™) blocks the activity of the Bcr-Abl oncoprotein and the cell transmembrane tyrosine kinase receptor c-Kit. Glivec™ is approved for several indications including the treatment on chronic myeloid leukemia (CML) and gastrointestinal stromal tumors (GIST).

Nilotinib and the process for its manufacture are disclosed in WO 04/005281, which is hereby incorporated by reference.

Pharmaceutically acceptable salts of nilotinib are especially those disclosed in WO2007/015871. In one preferred embodiment nilotinib is employed in the form of its hydrochloride monohydrate. WO2007/015870 discloses certain polymorphs of nilotinib and pharmaceutically acceptable salts thereof suitable for the present invention.

Nilotinib and its pharmaceutically acceptable salts can be administered by any route including orally, parenterally, e.g., intraperitoneally, intravenously, intramuscularly, subcutaneously, intratumorally, or rectally, or enterally. Preferably, Nilotinib and its pharmaceutically acceptable salts are administered orally, preferably at a daily dosage of 100-2000 mg. A preferred oral daily dosage of nilotinib is 200-1200 mg, e.g. 800 mg, administered as a single dose or divided into multiple doses, such as twice daily dosing.

Usually, a small dose is administered initially and the dosage is gradually increased until the optimal dosage for the host under treatment is determined. The upper limit of dosage is that imposed by side effects and can be determined by trial for the host being treated.

Nilotinib (Tasigna™) is a second-generation protein tyrosine kinase inhibitor (PTKI) and was approved in 2007 for the treatment of adult patients with chronic-phase and accelerated-phase Philadelphia chromosome-positive (Ph+) CML, resistant to or intolerant of prior treatment that included imatinib. The compound is also being investigated for the treatment of patients with GIST.

The structure of the other active agents identified herein by code nos., generic or trade names may be taken from the actual edition of the standard compendium "The Merck Index" or from databases, e.g. Patents International (e.g. IMS World Publications). The corresponding content thereof is hereby incorporated by reference.

In a further aspect, the present invention concerns the use of PDGF-R inhibitors, or pharmaceutically acceptable salts thereof, respectively, for the manufacture of a medicament for treating lymphatic metastasis of gastric cancer.

The invention relates also to a method for administering to a mammal, especially a human patient, having gastric cancer a pharmaceutically effective amount of a PDGF-R inhibitor or a pharmaceutically acceptable salt thereof, respectively, to the mammal in need thereof.

The person skilled in the pertinent art is fully enabled to select a relevant test model to prove the hereinbefore and hereinafter indicated therapeutic indications and beneficial effects. The pharmacological activity is, for example, demonstrated in well established in vitro and in vivo test procedures.

The following Example illustrates the invention described above, but is not, however, intended to limit the scope of the invention in any way.

EXAMPLE 1

Expression Profile of PDGF-B and PDGF-Rβ in Human Gastric Carcinoma

Materials and Methods

Patients and tumor specimens. Endoscopic biopsy specimens (tumor and corresponding normal mucosa) of gastric tissue from 38 patients with gastric carcinoma who later underwent surgical resection at Hiroshima University Hospital were snap-frozen in liquid nitrogen and stored at −80° C. until RNA extraction for quantitative reverse transcription-polymerase chain reaction (RT-PCR). Informed consent was obtained from all patients for participation in the study according to the Declaration of Helsinki. Pathology reports and clinical histories were reviewed for accurate staging at the time of surgery. Criteria for staging and histologic classification were those proposed by the Japanese Research Society for Gastric Cancer (Japanese Research Society for Gastric Cancer. Japanese classification of gastric carcinoma. Tokyo: Kanehara; 1999). Lymph node status was determined by routine pathological examination with the surgical specimens. Two groups of patients, those with lymph node metastasis (node-positive group, n=21) and those without (node-negative group, n=17), were closely matched for histologic type and depth of invasion. The patient group comprised 34 men and 4 women with a median age of 66.5 years. All patients had invasive gastric carcinoma in which the tumor invasion was beyond the submucosa.

Cell cultures. Four cell lines established from human gastric carcinomas and human osteosarcoma cell line MG63 were maintained in RPMI 1640 (Nissui Co., Tokyo, Japan) with 10% fetal bovine serum (FBS; MA BioProducts, Baltimore, Md., USA). TMK-1 cell line (a poorly differentiated adenocarcinoma) was provided by Dr. E. Tahara of Hiroshima University. KKLS cell line (an undifferentiated carcinoma) was provided by Dr. Y. Takahashi of Chiba University, Chiba, Japan. Two other cell lines (MKN-1, from an adenosquamous carcinoma, and MKN-45, from a poorly differentiated adenocarcinoma) as well as MG63 were obtained from the Health Science Research Resources Bank, Osaka, Japan.

Quantitative real-time RT-PCR analysis. Total RNA was extracted from gastric carcinoma cell lines and biopsy specimens with an RNeasy Kit (Qiagen, Valencia, Calif., USA) according to the manufacturers instructions. cDNA was synthesised from 1 µg total RNA with a first-strand cDNA synthesis kit (Amersham Biosciences, Piscataway, N.J., USA). After reverse transcription of RNA into cDNA, quantitative RT-PCR was performed with a LightCycler-FastStart DNA Master SYBR-Green I Kit (Roche Diagnostics, Basel, Switzerland) according to the manufacturers recommended protocol. PCR reactions were carried out in triplicate. To correct for differences in both RNA quality and quantity between samples, values were normalised to those of β-actin. The mRNA ratio between gastric carcinoma tissues (T) and corresponding normal mucosa (N) was calculated and expressed as the T/N ratio. Primers for PCR were designed with specific primer analysis software (Primer Designer, Scientific and Educational Software, Durham, N.C., USA), and specificity of the sequences was confirmed by FASTA (EMBL Database). Respective primer sequences, annealing temperatures, and PCR cycles were as follows: PDGF-B forward, CGAGT-TGGACCTGAACATGA (SEQ ID NO:1) and PDGF-B reverse, GTCACCGTGGCCTTCTTAAA (SEQ ID NO:2) (PDGF-B PCR product, 339 bp; 58° C.; 35 cycles); PDGF-Rβ forward, AGCTACCCCTCAAGGAATCATAG (SEQ ID NO:3) and PDGF-Rβ reverse, CTCTGGTGGATGGAT-TAAGACTG (SEQ ID NO:4) (PDGF-Rβ PCR product, 376 bp; 58° C.; 35 cycles); and GAPDH forward, ATCATCCCT-GCCTCTACTGG (SEQ ID NO:5) and GAPDH reverse, CCCTCCGACGCCTGCTTCAC (SEQ ID NO:6) (GAPDH PCR product, 188 bp; 55° C.; 28 cycles).

Reagents. Imatinib mesylate was diluted in sterile water for oral administration. Primary antibodies were purchased from as follows: polyclonal rabbit anti-PDGF-Rβ and polyclonal rabbit anti-PDGF-B subunit from Santa Cruz Biotechnology (Santa Cruz, USA); rat anti-mouse Lyve-1 from R&D Systems (Minneapolis, Minn., USA).

Western blot analysis. After three washes with cold phosphate-buffered saline (PBS) containing 1 mmol/L sodium orthovanadate, cells were lysed. Proteins (total protein 20 µg) were separated by SDS-PAGE and transferred to nitrocellulose transfer membranes (Whatman GmbH, Germany). The immune complexes were visualised by enhanced chemiluminescence with an ECL Plus Kit (GE Healthcare, Buckinghamshire, UK).

Animals and orthotopic implantation of tumor cells. Male athymic BALB/c nude mice (Charles River Japan, Tokyo) were maintained under specific pathogen-free conditions and used at 5 weeks of age. Subconfluent gastric cancer cells (TMK-1 or KKLS cells) to be used for implantation were harvested by brief treatment with 0.25% trypsin and 0.02% ethylenediamine tetraacetic acid, and then re-suspended to a final concentration of $2.0 \times 10^7$ cells/mL Hanks' solution. With the use of a 30-gauge needle attached to a 1-mL syringe, cells ($1 \times 10^6$ cells in 50 µl) were implanted into the gastric walls in the nude mice under observation with a zoom stereomicroscope. After 4 weeks, the mice were killed, and the tumors were resected for study. The tumors were embedded in OCT compound (Miles, Elkhart, Ind., USA), rapidly frozen in liquid nitrogen, and stored at −80° C.

Immunofluorescence staining for PDGF-B and PDGF-Rβ, and double staining for PDGF-Rβ and Lyve-1. Fresh frozen specimens of human gastric carcinomas as well as human gastric carcinomas growing in nude mice were cut into 8-µm sections, mounted on positively charged slides, and stored at −80° C. Tissue sections were fixed in cold acetone for 10 minutes and then washed 3 times with PBS for 3 minutes each. Slides were placed in a humidified chamber and incubated with protein blocking solution (5% normal horse serum and 1% normal goat serum in PBS) for 20 minutes at room temperature. The slides were incubated overnight at 4° C. with primary antibody against PDGF-B or PDGF-Rβ, then rinsed 3 times with PBS, incubated for 10 minutes in protein blocking solution and incubated for 1 hour at room temperature with Cy3-conjugated goat anti-rabbit secondary antibody. From this point onwards, the slides were protected from light. The samples were then rinsed 3 times in PBS. To identify lymph endothelial cells, slides were incubated overnight at 4° C. with antibody against Lyve-1. The sections were rinsed 3 times with PBS and incubated for 10 minutes in protein blocking solution. Slides were then incubated for 1 hour at room temperature with corresponding Cy5-conjugated secondary antibody, and the samples were rinsed 3 times in PBS. DAPI nuclear counterstain was applied for 10 minutes. Samples were then rinsed 3 times with PBS, and mounting medium was placed on each sample, which was then covered with a glass coverslip. Fluoromount/Plus (Diagnostic Bio Systems, Pleasanton, USA) was used as mounting medium.

Confocal microscopy. Confocal fluorescence images were obtained at ×203 or ×403 magnification on a Zeiss LSM 510 laser scanning microscopy system (Carl Zeiss, Thornwood, N.Y.) equipped with a motorised Axioplan microscope, argon laser (458/477/488/514 nm, 30 mW), HeNe lasers (543 nm, 1 mW; 633 nm, 5 mW), LSM 510 control and image acquisition software, and appropriate filters (Chroma Technology Corp., Brattleboro, Vt., USA). Lymphatic endothelial cells were identified by green fluorescence, whereas PDGF and PDGF-R were identified by red fluorescence.

Figure 3:
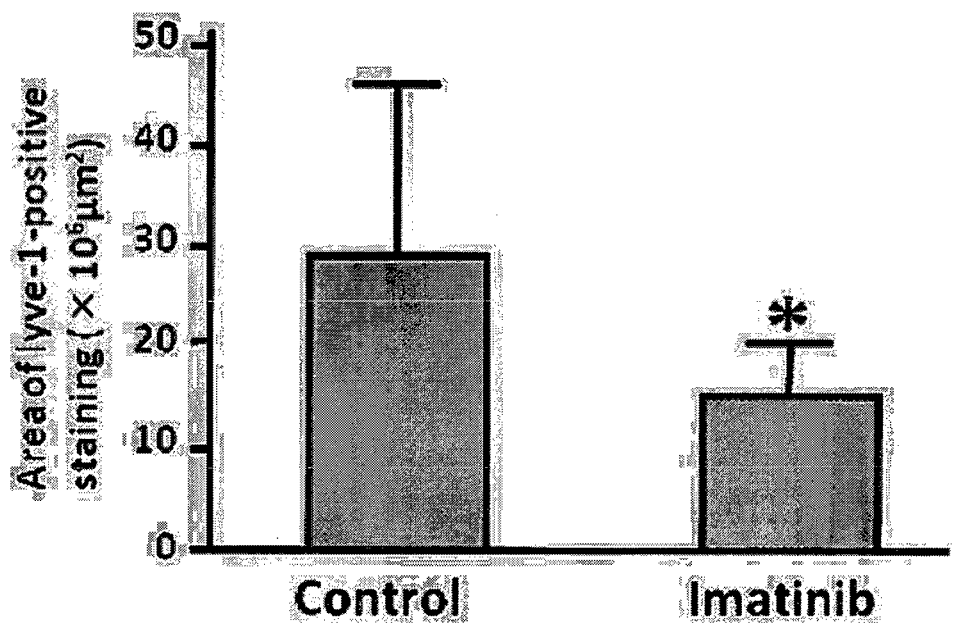
FIG. 3 Immunohistochemistry for Lyve-1 in TMK-1 orthotopic gastric tumors with and without imatinib treatment. Treatment with imatinib significantly reduced the area of lymphatic vessels. *P<0.05; bars, SE.

Treatment of established human gastric cancer tumors growing in murine gastric walls. Fourteen days after orthotopic implantation of TMK-1 cells, mice (n=10 each group) were randomly assigned to receive one of the following two treatments daily oral gavage of water (control group) or daily oral gavage of imatinib mesylate (50 mg/kg, optimal biological dose as determined previously (Hwang R F, et al. Clin Cancer Res 2003; 9: 6534-44) The treatments continued for 28 days. All therapy experiments were performed twice. The mice bearing orthotopic tumors were euthanised by methophane on day 29. For immunohistochemistry, the tumor tissues were fixed in formalin and embedded in paraffin. Results are shown in FIG. 3.

Immunohistochemical determination of the area of lymphatic vessels. Paraffin-embedded tissues were used for immunohistochemical identification of Lyve-1. Sections were deparaffinised and rehydrated in PBS, microwaved in water for 5 minutes for antigen retrieval, incubated overnight at 4° C. with mouse anti-Lyve-1 antibody, and incubated for 1 hour at room temperature with a peroxidase-conjugated rat anti-mouse antibody. A positive reaction was detected by exposure to stable 3,3'-diaminobenzidine for 5-10 minutes. Slides were counterstained with Gill's hematoxylin. On slides immunolabeled for Lyve-1, only vessels with typical morphology (including a lumen) were counted as lymphatic vessels because of occasional weak antibody cross-reactivity with fibroblasts (Valencak J, et al., Eur J Cancer 2004; 40: 358-64. For quantification of the lymphatic vessel areas, 10 random fields at ×100 magnification were captured for each tumor, and the outline of each lymphatic vessel including a lumen was manually traced. The areas were then calculated with the use of NIH ImageJ software (http://rsbweb.nih.gov/ij/download.html).

Statistical analysis. Results are expressed as mean±SE. Wilcoxon/Kruskal-Wallis analysis was used to analyze between-group differences in continuous variables. A P value of less than 0.05 was considered statistically significant.

The invention claimed is:

1. A pharmaceutical composition comprising a PDGF-R inhibitor, wherein the PDGF-R inhibitor is selected from the group consisting of 4-(4-methylpiperazin-1-ylmethyl)-N-[4-methyl-3-(4-pyridin-3-yl)pyrimidin-2-ylamino)phenyl]-benzamide, 4-methyl-3-[[4-(3-pyridinyl)-2-pyrimidinyl]amino]-N-[5-(4-methyl-1H-imidazol-1-yl)-3-(trifluoromethyl)phenyl]benzamide, and N-(2-diethylaminoethyl)-5-[(Z)-(5-fluoro-2-oxo-1H-indol-3-ylidene)methyl]-2,4-dimethyl-1H-pyrrole-3-carboxamide or pharmaceutically acceptable salts thereof, respectively.

2. The pharmaceutical composition of claim 1 wherein the PDGF-R inhibitor is 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof.

3. The pharmaceutical composition of claim 2 wherein the PDGF-R inhibitor is 4-(4-methylpiperazin-1-ylmethyl)-N-[4-methyl-3-(4-pyridin-3-yl)pyrimidin-2-ylamino)phenyl]-benzamide mesylate.

4. The pharmaceutical composition of claim 1 wherein the PDGF-R inhibitor is 4-methyl-3-[[4-(3-pyridinyl)-2-pyrimidinyl]amino]-N-[5-(4-methyl-1H-imidazol-1-yl)-3-(trifluoromethyl)phenyl]benzamide or a pharmaceutically acceptable salt thereof.

5. The pharmaceutical composition of claim 4 wherein the PDGF-R inhibitor is 4-methyl-3-[[4-(3-pyridinyl)-2-pyrimidinyl]amino]-N-[5-(4-methyl-1H-imidazol-1-yl)-3-(trifluoromethyl)phenyl]benzamide hydrochloride monohydrate.

6. The pharmaceutical composition of claim 1 wherein the PDGF-R inhibitor N-(2-diethylaminoethyl)-5-[(Z)-(5-fluoro-2-oxo-1H-indol-3-ylidene)methyl]-2,4-dimethyl-1H-pyrrole-3-carboxamide, or a pharmaceutically acceptable salt thereof.

* * * * *